United States Patent [19]

Annen et al.

[11] Patent Number: 5,763,639
[45] Date of Patent: Jun. 9, 1998

[54] PROCESS FOR PRODUCING QUARTERNARY GLYCINE NITRILES

[75] Inventors: Ulrich Annen, Hassloch; Hans-Peter Seelmann-Eggebert, Limburgerhof; Rudi Widder, Leimen; Reinhard Müller, Friedelsheim, all of Germany

[73] Assignee: BASF Aktiengesellschaft, Ludwigshafen, Germany

[21] Appl. No.: 793,448

[22] PCT Filed: Aug. 17, 1995

[86] PCT No.: PCT/EP95/03273

§ 371 Date: Mar. 3, 1997

§ 102(e) Date: Mar. 3, 1997

[87] PCT Pub. No.: WO96/07650

PCT Pub. Date: Mar. 14, 1996

[30] Foreign Application Priority Data

Sep. 2, 1994 [DE] Germany .......................... 44 31 212.1

[51] Int. Cl.⁶ .................. C07C 209/60; C07C 211/08; C07C 255/03; C07C 255/33
[52] U.S. Cl. .................. 558/351; 558/371; 558/378; 558/388; 558/389; 558/390; 558/408; 564/282; 564/291; 564/296
[58] Field of Search ................. 558/371, 378, 558/388, 389, 408, 351, 390; 564/296

[56] References Cited

U.S. PATENT DOCUMENTS

| | | |
|---|---|---|
| 4,022,815 | 5/1977 | Schlecht et al. . |
| 4,113,764 | 9/1978 | Distler et al. . |
| 4,134,889 | 1/1979 | Distler et al. . |

FOREIGN PATENT DOCUMENTS

| | | |
|---|---|---|
| 049 577 | 9/1981 | European Pat. Off. . |
| 0 049 577 | 4/1982 | European Pat. Off. . |
| 458 396 | 5/1991 | European Pat. Off. . |
| 464 880 | 5/1991 | European Pat. Off. . |
| 0 458 396 | 11/1991 | European Pat. Off. . |
| 0 464 880 | 1/1992 | European Pat. Off. . |
| 25 03 582 | 8/1976 | Germany . |
| 25 55 769 | 6/1977 | Germany . |
| 26 20 445 | 11/1977 | Germany . |

OTHER PUBLICATIONS

The Journal of the American Chemical Society, vol. LV1, Jul.–Dec. 1934, Editor Arthur B. Lamb.

*Primary Examiner*—Johann Richter
*Assistant Examiner*—Jane C. Osowecki
*Attorney, Agent, or Firm*—Oblon, Spivak, McClelland, Maier & Neustadt, P.C.

[57] ABSTRACT

A process for preparing quaternized glycine nitriles of formula I

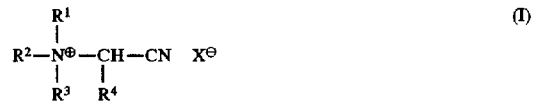

comprising reaction of the corresponding precursor amine, aldehyde, hydrocyanic acid or alkali metal cyanide, and subsequent quaternization with an alkylating agent, wherein the reaction and quaternization are carried out successively in aqueous medium without isolation of an intermediate.

4 Claims, No Drawings

PROCESS FOR PRODUCING QUARTERNARY GLYCINE NITRILES

This application is a 371 of PCT/EP95/03273 of Aug. 17, 1995.

BACKGROUND OF THE INVENTION

1. Field of the Invention

The present invention relates to an improved process for preparing quaternized glycine nitriles of the general formula I

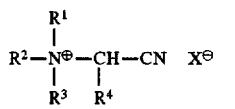

where

- $R^1$ and $R^2$ can be identical or different and are each an aliphatic, cycloaliphatic or araliphatic radical having from 1 to 30 carbon atoms, with $R^1$ and $R^2$ also being able to form, together with the nitrogen atom to which they are bound, a saturated or unsaturated five-membered or six-membered heterocyclic ring which can additionally contain further hetero atoms, can be benzo-fused and can bear alkyl side groups, and furthermore $R^2$ can also be hydrogen,
- $R^3$ is $C_1$- to $C_4$-alkyl or benzyl,
- $R^4$ is hydrogen, $C_1$- to $C_{20}$-alkyl which can be interrupted by one or more non-adjacent oxygen atoms, or a radical of the formula $$-R^5-CH-\overset{\overset{\displaystyle CN}{|}}{\underset{\underset{\displaystyle R^3}{|}}{N^\oplus}}-R^2 \quad X^\ominus$$

where $R^5$ is a chemical bond or a $C_1$- to $C_6$-alkylene bridge, and $X^\ominus$ is a counter ion, reaction of amines of the general formula II

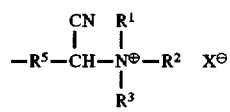

where the variables $R^1$ and $R^2$ are as defined above, with a monoaldehyde of the general formula IIIa or a dialdehyde of the general formula IIIb $$R^6-CHO \quad \text{(IIIa)}$$

$$OHC-R^5-CHO \quad \text{(IIIb)}$$

where $R^5$ is as defined above and $R^6$ is hydrogen or $C_1$- to $C_{20}$-alkyl, and hydrocyanic acid or an alkali metal cyanide in aqueous medium and subsequent quaternization with an alkylating agent of the general formula IV $$R^3-X \quad \text{(IV)}$$

where $R^3$ is as defined above and X is a leaving group.

2. Discussion of the Background

The patents U.S. Pat. Nos. 5,236,616 (1) and 5,281,361 (2) disclose cationic nitriles containing, for example, the structural unit

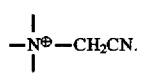

Cationic nitriles, e.g. $(CH_3)_3N^\oplus-CH_2CN \; Cl^\ominus$, are presented there as extremely hygroscopic, i.e. water-sensitive substances, which rapidly take up water from the air and can easily hydrolyze to give corresponding amides. Cationic nitriles are therefore generally (prepared in anhydrous organic solvents, e.g. in dry acetonitrile (cf. Example 1(i) of (1)).

SUMMARY OF THE INVENTION

It is an object of the present invention to provide a preparation process for cationic nitriles or formulations thereof, which gives products which do not have such water sensitivity.

We have found that this object is achieved by the process defined in the introduction, wherein the reaction of the amines II with the aldehydes III and hydrocyanic acid or alkali metal cyanide and the quaternization are carried out successively in aqueous medium without isolation of an intermediate.

This gives aqueous solutions of the quaternized glycine nitriles I described, which have virtually unlimited stability under usual conditions, i.e. are not sensitive to hydrolysis. When storing the aqueous solutions of the quaternized glycine nitriles I prepared according to the invention, usually no hydrolysis products are found even after a period of several weeks at temperatures of up to 40° C.

DETAILED DESCRIPTION OF THE PREFERRED EMBODIMENTS

The unquaternized glycine nitrile I precursors, which are not isolated or even purified in the process of the invention, and their preparation are known in principle from the patents DE-A 25 03 582 (3), DE-A 25 55 769 (4) and DE-A 26 20 445 (5).

The radicals $R^1$ and $R^2$ are each preferably $C_1$- to $C_{18}$-alkyl, particularly preferably $C_2$- to $C_{10}$-alkyl, more preferably $C_3$- to $C_{10}$-cycloalkyl, especially $C_5$- to $C_7$-cycloalkyl, or furthermore, in particular, araliphatic radicals having from 7 to 20 carbon atoms, especially phenylalkyl having from 7 to 12 carbon atoms.

Suitable heterocyclic ring structures containing $R^1$ and $R^2$ are, in particular, those which contain, besides the nitrogen atom of the glycine moiety, no, one or two further hetero atoms from the group consisting of nitrogen or oxygen. The heterocyclic rings preferably bear no, one or two fused benzene rings. If additional alkyl side groups are present, these are preferably $C_1$- to $C_4$-alkyl, in particular methyl or ethyl.

In accordance with the specified meanings of $R^1$ and $R^2$, the following primary or secondary amines II can be used with particularly good results as starting compounds in the process of the invention:

methylamine, ethylamine, n-propylamine, isopropylamine, n-butylamine, isobutylamine, sec-butylamine, tert-butylamine, pentylamine, pentyl-(2)-amine, pentyl-(3)-amine, n-hexylamine, n-heptylamine, n-octylamine, n-nonylamine, n-decylamine, 2,2,6-trimethyl-n-pentylamine, 2-ethylpentylamine, 3-ethylpentylamine, 2,3-di-methyl-n-butylamine, 2,2-dimethyl-n-butylamine, 2-methylpentylamine, 3-methylpentylamine, 2,2,4-trimethylpentylamine, 2-methylheptylamine, 3-methylheptylamine, 4-methylheptylamine, 2-ethylhexylamine, 3-ethylhexylamine, 2,2-dimethylhexylamine, 2,3-dimethylhexyl-amine, 2,4-dimethylhexylamine, 2,5-dimethylhexylamine, 3,3-dimethylhexylamine, 3,4-dimethylhexylamine, 2-methyl-3-ethylpentylamine, 3-methyl-3-ethylpentylamine, 2,2,3-trimethylpentyl-amine, 2,2,4-trimethylpentylamine, 2,3,3-trimethylpentylamine, 2,3,4-trimethylpentylamine, 2,2,3,3-tetramethylbutyl-amine; di(methyl)amine, di(ethyl)amine, di(n-propyl)amine, di(isopropyl)amine, di(n-butyl)amine, di(isobutyl)amine, di(secbutyl)amine, di(tert-butyl)amine, di(pentyl)amine, di(pentyl)-(2)-amine, di(pentyl)-(3)-amine, di(n-hexyl)amine, di(n-heptyl)amine, di(n-octyl)amine, di(n-nonyl)amine, di(n-decyl)amine, di(2,2,6-trimethyl-n-pentyl)amine, di(2-ethylpentyl)amine, di(3-ethylpentyl)amine, di(2,3-dimethyl-n-butyl)amine, di(2,2-dimethyl-n-butyl)amine, di(2-methylpentyl)amine, di(3-methylpentyl)amine, di(2,2,4-trimethylpentyl)amine, di(2-methylheptyl)amine, di(3-methylheptyl)amine, di(4-methylheptyl)amine, di(2-ethylhexyl)amine, di(3-ethylhexyl)amine, di(2,2-dimethylhexyl)amine, di(2,3-dimethylhexyl)amine, di(2,4-dimethylhexyl)amine, di(2,5-dimethylhexyl)amine, di(3,3-dimethylhexyl)amine, di(3,4-dimethylhexyl)amine, di(2-methyl-3-ethylpentyl) amine, di (3-methyl-3-ethylpentyl) amine, di(2,2,3-trimethylpentyl)amine, di(2,2,4-trimethylpentyl)amine, di(2,3,3-trimethylpentyl)amine, di(2,3,4-trimethylpentyl)amine, di(2,2,3,3-tetramethylbutyl) amine;
corresponding aliphatic amines containing two of the above, but different, radicals, e.g. methylethylamine;
cyclohexylamine, cyclopentylamine, cycloheptylamine, benzylamine, phenylethylamine;
dicyclohexylamine, dicyclopentylamine, dicycloheptylamine, dibenzylamine, diphenylethylamine; pyrrolidine, $\Delta^2$-pyrroline, $\Delta^3$-pyrroline, pyrrole, pyrazole, pyrazoline, pyrazolidine, imidazolidine, hexamethylenimine, 3-imidazoline, piperidine, piperazine, indoline, indole, isoindoline, isoindole, indazole, benzimidazole, 1,2,3,4-tetrahydroisoquinoline, carbazole, phenoxazine, 4-methylimidazole, 2-methylindole, 3-methylindole, 2-methylpiperazine, 3-methylpyrrole, 2-methylpyrrole, 2-ethylpiperidine, 2-methylpyrrolidine.

Suitable alkylating agents IV, which are responsible for the introduction of the group $R^3$, are, in particular, dimethyl sulfate, diethyl sulfate, a methyl or ethyl halide, dimethyl carbonate, diethyl carbonate, methyl tosylate, ethyl tosylate, methyl mesylate, ethyl mesylate or a benzyl halide. For the purposes of the present invention, a halide is chloride, bromide or iodide. Accordingly, the preferred meanings for the leaving group X or the counter ion $X^\ominus$ are $CH_3OSO_3$, $C_2H_5OSO_3$, Cl, Br, I, $CH_3OCO_2$, $C_2H_5OCO_2$, p-tolyl-$SO_3$ and $CH_3SO_3$. Preferred meanings of $R^3$ are accordingly methyl, ethyl and benzyl.

The radical $R^4$, which originates from the aldehyde component III, is preferably hydrogen, corresponding to the starting compound being formaldehyde as compound IIIa. However, it is also possible to use $C_2$- to $C_{21}$-alkanals, in particular $C_2$- to $C_7$-alkanals, as compounds IIIa, e.g. acetaldehyde, propionaldehyde or butyraldehyde. If dialdehydes IIIb such as glyoxal, malonodialdehyde, succinodialdehyde, glutarodialdehyde, 3-oxaglutarodialdehyde or adipodialdehyde are used, doubling of the glycine nitrile structure generally occurs with appropriate stoichiometric ratios.

The reaction of the amines II with the aldehydes III and hydrocyanic acid or alkali metal cyanide to give the unquaternized glycine nitriles I in aqueous medium is known in principle from the patents (3) to (5). The reaction is normally carried out at temperatures of from 0° to 80°C., preferably from 20° to 65° C., particularly preferably from 30° to 55° C., and at atmospheric pressure. The reaction is usually complete after from 4 to 6 hours.

The subsequent quaternization by means of the alkylating agent IV is generally carried out in the same temperature and pressure range.

The preparation of the products I by reaction of the amines II and by quaternization, which is configured as a "single-vessel reaction" according to the invention, is advantageously carried out either in pure aqueous solution or a mixture of water and up to 30% by weight, preferably up to 15% by weight, particularly preferably up to 5% by weight, based on the mixture, of a water-miscible organic solvent, for example an alcohol such as methanol, ethanol or isopropanol.

EXAMPLE

Preparation of N-methylpiperidiniumacetonitrile methosulfate

A stirred vessel is initially charged with 341 g (4 mol) of piperidine. At 40° C., 400 g (4 mol) of a 30% strength by weight aqueous formaldehyde solution and 108 g (4 mol) of hydrocyanic acid were metered in simultaneously over a period of 2 hours. After stirring further for 1 hour at 40° C., 504 g (4 mol) of dimethyl sulfate were quickly added at the same temperature and the mixture stirred for a further 2 hours at 40° C. Dimethyl sulfate could no longer be detected in the solution obtained.

We claim:

1. A process for preparing quaternized glycine nitriles of the general formula I

where $R^1$ and $R^2$ may be identical or different and are each an aliphatic, cycloaliphatic or araliphatic radical having from 1 to 30 carbon atoms, with $R^1$ and $R^2$ also being able to form, together with the nitrogen atom to which they are bound, a saturated or unsaturated five-membered or six-membered heterocyclic ring which may additionally contain further hetero atoms, may be benzo-fused and may bear alkyl side groups, and furthermore $R^2$ may also be hydrogen, $R^3$ is $C_1$- to $C_4$-alkyl or benzyl, $R^4$ is hydrogen, $C_1$- to $C_{20}$-alkyl which may be interrupted by one or more non-adjacent oxygen atoms, or a radical of the formula

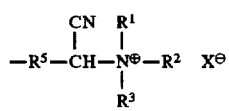

where $R^5$ is a chemical bond or a $C_1$- to $C_6$-alkylene bridge, and $X^\ominus$ is a counter ion, by reaction of an amine of the general formula II

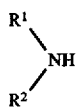 (II)

where the variables $R^1$ and $R^2$ are as defined above, with a monoaldehyde of the general formula IIIa or a dialdehyde of the general formula IIIb

 (IIIa),

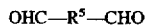 (IIIb)

where $R^5$ is as defined above and $R^6$ is hydrogen or $C_1$- to $C_{20}$-alkyl, and either of which provides the variable $R^4$ in Formula I and hydrocyanic acid or an alkali metal cyanide in aqueous medium and subsequent quaternization with an alkylating agent of the general formula IV

 (IV)

where $R^3$ is as defined above and X is a leaving group, wherein the reaction of the amine II with the aldehyde III and hydrocyanic acid or alkali metal cyanide and the quaternization are carried out successively in aqueous medium without isolation of an intermediate.

2. A process for preparing quaternized glycine nitriles I as claimed in claim 1, in which $R^4$ is hydrogen.

3. A process for preparing quaternized glycine nitriles I as claimed in claim 1, wherein the alkylating agent IV used is dimethyl sulfate, diethyl sulfate, a methyl or ethyl halide, dimethyl carbonate, diethyl carbonate, methyl tosylate, ethyl tosylate, methyl mesylate, ethyl mesylate or a benzyl halide.

4. A process for preparing quaternized glycine nitriles I as claimed in claim 1, wherein the reaction of the amines II and the quaternization are carried out in pure aqueous solution or a mixture of water and up to 30% by weight, based on the mixture, of a water-miscible organic solvent.

* * * * *